United States Patent [19]

Rossi et al.

[11] Patent Number: 6,069,007
[45] Date of Patent: *May 30, 2000

[54] RIBOZYME CLEAVAGE OF HIV RNA

[75] Inventors: John J. Rossi, Glendora; Edouard M. Cantin, Los Angeles; John A. Zaia, Arcadia; Pairoj Chang, San Dimas, all of Calif.

[73] Assignee: City of Hope, Duarte, Calif.

[ * ] Notice: This patent is subject to a terminal disclaimer.

[21] Appl. No.: 07/798,128

[22] Filed: Nov. 26, 1991

Related U.S. Application Data

[60] Division of application No. 07/401,613, Aug. 31, 1989, abandoned, which is a continuation-in-part of application No. 07/369,489, Jun. 21, 1989, Pat. No. 5,144,019.

[51] Int. Cl.$^7$ .............................. C07H 21/04; C12Q 1/68; C12N 15/00; C12N 15/85
[52] U.S. Cl. ........................... 435/367; 435/6; 435/91.31; 435/320.1; 435/325; 435/366; 435/375; 536/23.1; 536/23.2; 536/24.31; 536/24.33; 536/24.5
[58] Field of Search .................................. 435/455, 320.1, 435/375, 6, 325, 366, 367, 91.31; 536/23.1, 24.31, 23.2, 24.33, 24.5

[56] References Cited

PUBLICATIONS

Barinaga Science 262: 1512–1514 (1993).
Johnston et al. Science 260: 1286–1293 (1993).
Gerlach et al. J. Cell. Biochem. Suppl. 12C, 239, 1988.
Rossi et al. J. Cell. Biochem. Suppl. 13B, G329, 1989.

*Primary Examiner*—John L. LeGuyader
*Assistant Examiner*—Jane Zara
*Attorney, Agent, or Firm*—Rothwell, Figg, Ernst & Kurz

[57] ABSTRACT

Ribozymes useful to cleave HIV-1 and other viral or endogenous cellular RNAs are disclosed. Also disclosed are transformed cells which express such ribozymes and human AIDS therapy involving the administration of such ribozymes.

10 Claims, 6 Drawing Sheets

RIBOZYME CLEAVAGE OF HIV RNA

This is a division of application Ser. No. 401,613 filed Aug. 31, 1989, now abandoned, which is a continuation-in-part of pending application Ser. No. 369,489 filed Jun. 21, 1989 now U.S. Pat. No. 5,144,019.

This invention was made with government support under Grant No. J.R. NIAID R01 AI29329 awarded by the National Institutes of Health. The government has certain rights in the invention.

FIELD OF THE INVENTION

This invention relates to ribozymes effective to cleave HIV-1 RNA and other viral and endogenous cellular RNA. More particularly, the invention relates to cells transformed with such ribozymes, and to anti-AIDS therapy including the administration of such ribozymes to mammalian patients including humans.

BACKGROUND OF THE INVENTION

One form of gene expression impairment by RNA-RNA duplex formation has been termed "antisense" inhibition. This approach to viral therapy is stoichiometric and may require large molar excesses of anti-sense versus target RNA to be effective.

Ribozymes provide antisense molecules which form RNA-RNA hybrids and catalytically cleave the covalent phosphodiester linkages. Ribozymes can be targeted to many RNA transcripts, and efficient cleavage can be achieved in vitro. See, Kim, S. H., et al. *Proc. Natl Acad. Sci. U.S.A.* 84:8788–8792 (1987); Haseloff, J., et al., *Nature* 234:585–591 (1988); Cech, T. R. *JAMA* 260:3030–3034 (1988); Jeffries, A. G., et al., *Nucleic Acids Research* 17:1371–1377 (1989).

Haseloff, et al. developed a set of rules useful to design transacting ribozymes. The utility of these rules was demonstrated in vitro by ribozymes effectively targeted to different sites within the chloramphenicol acetyltransferase transcript. Haseloff, et al. state that "A major potential application for these highly sequence specific endoribonucleases is in cleavage and thereby inactivation of gene transcripts in vivo. . . . Provided that the transcribed sequences of the gene are known, it should be possible to target one or more ribozymes against specific RNA transcripts. Expression in vivo of such ribozymes and cleavage of the transcripts would in effect inhibit expression of the corresponding gene. This 'auto-gene' activity of the ribozymes could provide a basis for various gene and viral therapies and analyses" (pp. 590–591).

SUMMARY OF THE INVENTION

This invention provides stable, catalytically efficient ribozymes useful, inter alia, to cleave HIV-1 RNA or any other viral or endogenous cellular RNA, in vitro and in vivo, and transformed cells which express such ribozymes. Human AIDS therapy involving the administration of such ribozymes and transformed cells is an important aspect of the invention.

DETAILED DESCRIPTION OF THE INVENTION

The mechanism of ribozyme cleavage requires highly conserved sequences which include a target or substrate RNA strand having a cleavage site and a catalytic RNA strand. Either the substrate strand, see, e.g., FIGS. 1 and 3, or the catalytic strand, see, e.g., FIGS. 2, 4, and 5, of the ribozymes useful in this invention include the conserved sequences GAAAC(X)$_n$GUE, in which X is any nucleotide, E is C, U or A, but not G, and n may have any value. Preferably, the value of n is from 0 to about 50. The sequence GUE provides a cleavage site. Preferred cleavage sites are preceded by the trinucleotides GUC or GUU.

One aspect of this invention includes predesigned, synthetic, catalytic strands specifically targeted to regions of HIV-1 RNA which include such substrate units. This aspect of the invention is exemplified by synthetic catalytic strands which include the core sequence 3' YGCNGUCZ 5' in which N is any nucleotide with 3' and 5' flanking sequences Y and Z of at least about 5, preferably at least about 5 to about 15, nucleotides complementary to target sequences adjacent the cleavage site.

Eleven GAAAC (X)$_n$ GUE substrate units in the HIV-1 HXB-2 isolate, see Rattner, L., et al., *Nature* 313:277–284 (1985), are set forth in Table I.

TABLE I

| Unit No. | RNA Sequence |
|---|---|

1. 5' pppGCGCC<u>GAAAC</u>ACCGUG<u>UC</u>UCGAGC-OH 3'       ↓Cleavage Site (above UC)

2. 5'CA<u>GAAAC</u>CUUGUUG<u>GUC</u>CAAAAUGCGAACC 3'       or Cleavage Sites ↓ ↓

3. 5'AAUCCUGGCCUGUUA<u>GAAAC</u>AUCAGAAGGCU<u>GUA</u>GACAAAAUACUGGGACAGCU-3'       ↓Cleavage site 4.    2411  
   CAGGAACAUG<u>GAAAC</u>CAAAAAUGAUAGGGGGAAUUGGAG<u>GUU</u>UUAUCAAAGUAAGACAGU       Cleavage Site ↓

5.    3768  
   AUACAAAAG<u>GAAAC</u>AUGGGAAACAUGGUGGACAGA<u>GUA</u>UU       Cleavage Site ↓

6.    3777  
   CCCAUACAAAAG<u>GAAAC</u>AUGGGAAACAUGGUGGACAGA<u>GUA</u>UUGGCAAGCC       Cleavage site ↓

7.    3894  
   UAGUAGGAGCA<u>GAAAC</u>CUUCUAU<u>GUA</u>GAUGGGGCAG       Cleavage Site ↓

8. & 9.    4536 and 4548  
   GUUAUUCCAGCA<u>GAAAC</u>AGGGCA<u>GAAAC</u>AGCAUAUUUUCUUUUAAAAUUAGCAGGAAGAU  
   GGCCA<u>GUA</u>AAAACAAU  
      ↑_____Cleavage Site 10.    5574  
    CCUAGUGUUAC<u>GAAAC</u>UGACAGAGGAUAGAUGGAACAAGCCCCAGAAGACCAAGGGCCACA  
    GAGGGAGCCACACAAUGAAUGGACACUAGAGCUUUUAGAGGAGCUUAAGAAUGAAGCU<u>GUU</u>  
    AGACAUUUUCCUA    ↑  
       Cleavage site 11.    5733  
    AACAUAUCUAU<u>GAAAC</u>UUAUGGGGAUACUUGGGCAGGAGUGGAAGCCAUAAUAAGAAUUCU  
    GCAACAACUGCU<u>GUU</u>UAUCCAUUUUCAGAA  
       ↑_____Cleavage site

EXAMPLE I

Ribozyme Transcription

The Ribozymes of FIGS. 1–3 and 5

Figure 5:
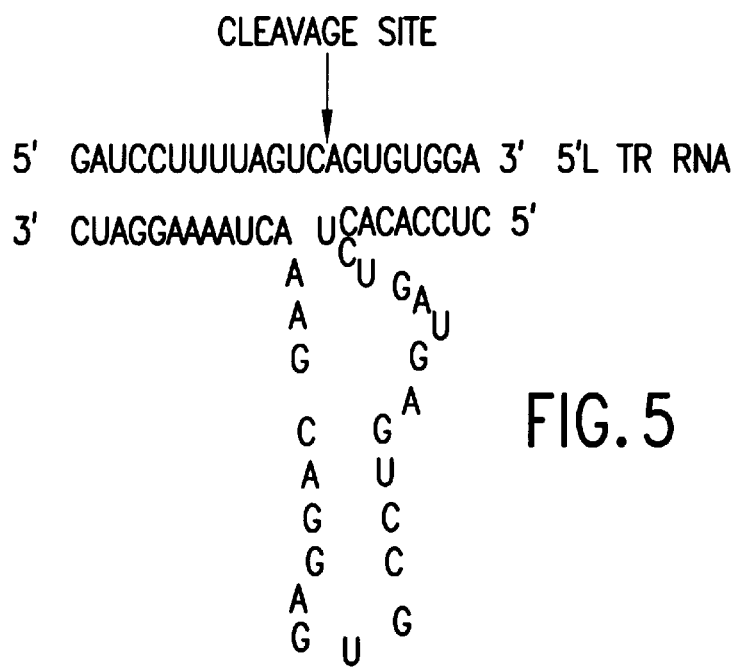
FIG. 5 illustrates a fifth ribozyme targeted to a cleavage site in the 5' LTR region of HIV-1.
Figure 6:
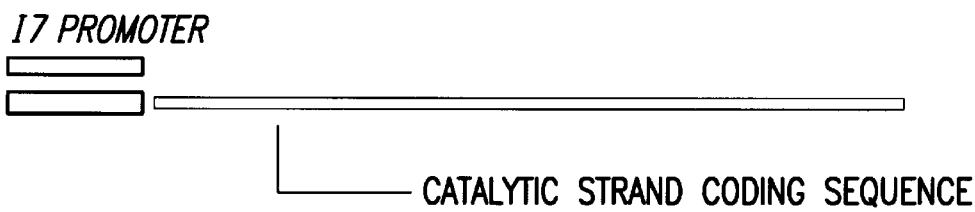
FIG. 6 is a schematic diagram indicating the hemi-duplex T-7 promoter construct used to transcribe the ribozymes illustrated by FIGS. 1 to 5.

The schematic diagram of FIG. 6 indicates the hemi-duplex T7 promoter template used to transcribe the ribozymes shown in FIGS. 1 to 3 and 5. The gag (FIGS. 1–3) or LTR (FIG. 5) template was transcribed from a T7 promoter using a cloned HIV-1 DNA segment in the Bluescript (Statagene) vector system. Several picomoles of template were incubated in a 20 microliter reaction containing 500 micro molar concentrations of ATP, CTP, and GTP, 50 micromolar concentration of UTP and 10 to 20 microcuries of $^{32}$P-labelled UTP (3000 Ci/mmole) in 40 mM Tris-HCl pH 8.0, 20 mM MgCl, 10 mM NaCl, 1 mM dithiothreitol and 20 units of placental ribonuclease inhibitor. Ten units of T7 RNA polymerase were added, and transcription allowed to proceed for 30 min. to 1 hour at 37° C. The reactions were terminated by phenol extraction, followed by ethanol precipitation, and the products purified by electrophoresis in a 6% or 10%, polyacrylamide-7M urea gel. The radioactive products were eluted by diffusion in sterile $H_2O$ and quantitated by counting in a scintillation counter set to monitor $^{32}$P.

Figure 4:
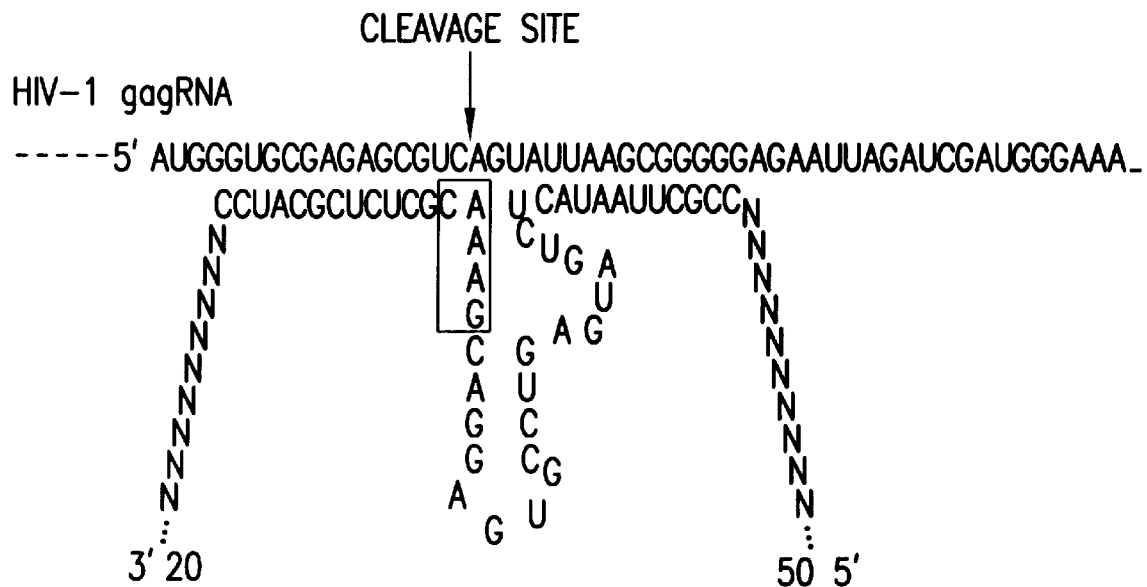
FIG. 4 illustrates a fourth ribozyme associated with yet another cleavage point in the gag region of HIV-1.

The Ribozyme of FIG. 4

Figure 7:
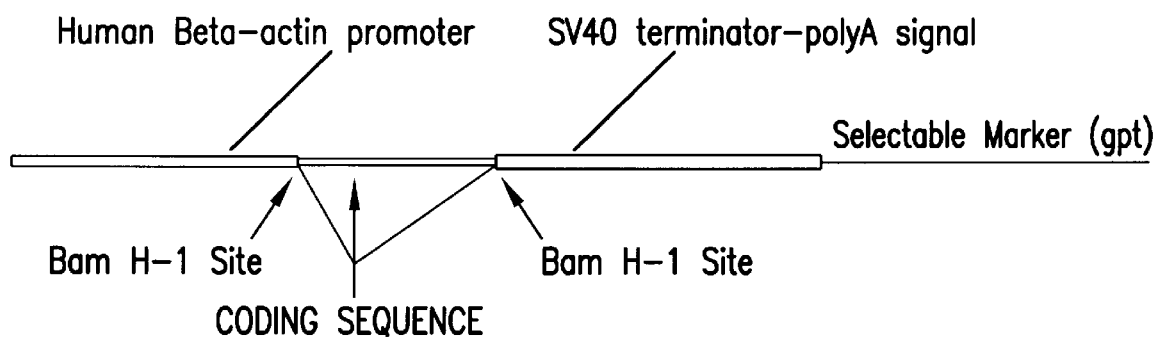
FIG. 7 illustrates a mammalian ribozyme expression vector.

The ribozyme gene depicted by FIG. 4 was first cloned into a Bluescript transcription vector and thereafter into the Bam H1 site of the mammalian expression vector depicted in FIG. 7.

More specifically, 20 picomoles of each of the oligonucleotides 5'CCGGATCCGCTTAATACTCTGATGAGTC-CTGTAGG 3' and 5'CCGGATCCGGTGC-GAGAGCGTTTCGTCCTACAGGAC 3' which have 10 bases of complementary sequence at their 3' termini, are mixed together in a 50 ul reaction containing the following: 50 mM KCl, 10 mM tris-HCl pH 8.3, 1.5 mM MgCl, 0.01% (w/v) gelatin, 200 uM each dnTP, 2.5 units of Taq DNA polymerase and the reaction mixture is overlain with 50 ul of mineral oil. The oligonucleotides are polymerized by cycling 10 times under the following conditions: 95° C. for 2', 45° C. for 2' and 72° C. for 3'. The product was electrophoresed in an 8% polyacrylamide gel. The polyacrylamide gel was stained with ethidium bromide (1 ug/ml), a gel slice containing the fragment was cut out, and the fragment was eluted by diffusion in 10 mM Tris pH 8.0, 1 mM EDTA.

The eluted double stranded DNA was then restricted with Bam H-1 to generate a fragment having cohesive termini for subsequent ligation to a similarly treated Bluescript bacterial plasmid vector. The DNA fragment was ligated with the Bluescript vector in known manner. The Bluescript vector was linearized with a restriction enzyme, e.g., Hind III or EcoRl, which cuts distal to the cloned ribozyme. The appropriate RNA polymerase, T7 or T3, is added in a standard transcription reaction to produce the RNA ribozyme as shown in FIG. 4 with 50 non-HIV-1 5' targeted and 20 non-HIV-1 3' targeted nucleotides. The extra nucleotides were derived from the polylinker sequences of the Bluescript vector.

The ribozyme was transformed into *E. coli* cells which were propagated, amplified and purified for subsequent use.

EXAMPLE II

Ribozyme Cleavage Reactions and Reaction Products

Figure 1:
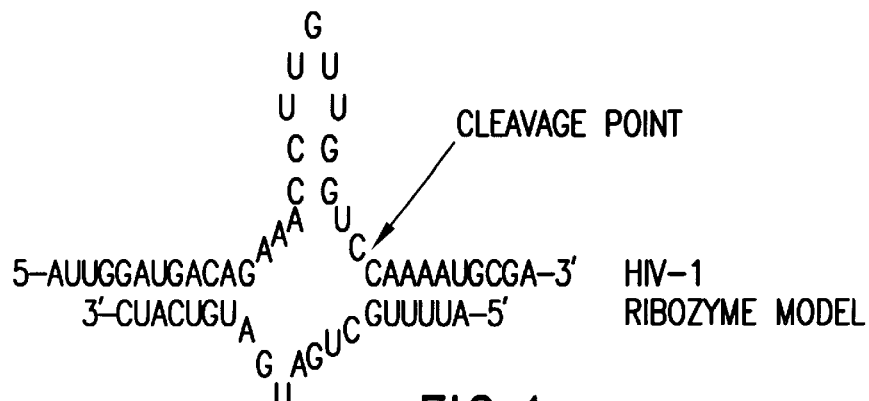
FIG. 1 illustrates a first ribozyme associated with a first cleavage point in the gag region of HIV-1.
Figure 2:
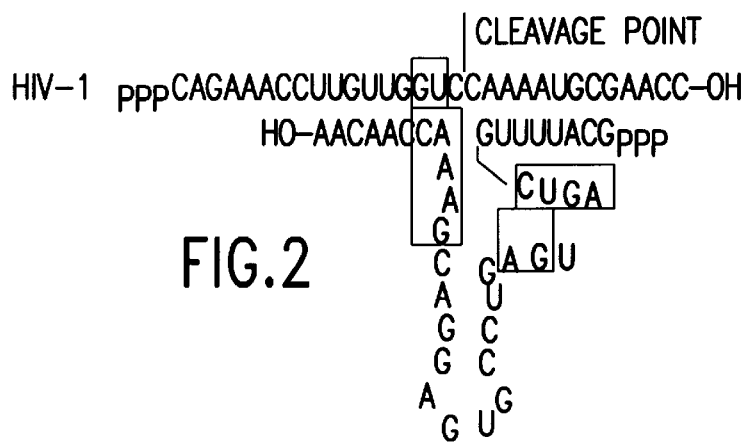
FIG. 2 illustrates the design of a second ribozyme associated with the same cleavage point in the gag region of HIV-1 as shown in FIG. 1.

Reaction conditions for the cleavage by the ribozymes of FIGS. 1, 2 and 5 were: ca. 1 pmole ribozyme in a 10 $\mu$l reaction containing 10 to 20 mM MgCl, 50 mM Tris-HCL pH 7.5, 1 mM EDTA. The RNA segments were heated to 90° C. briefly, quick-chilled in ice, the MgCl was then added and the reactions were brought to 37° C. for 14 hours. The reactions were stopped by the addition of an equal volume of 10M urea and EDTA to 12 mM final concentration.

Figure 8:
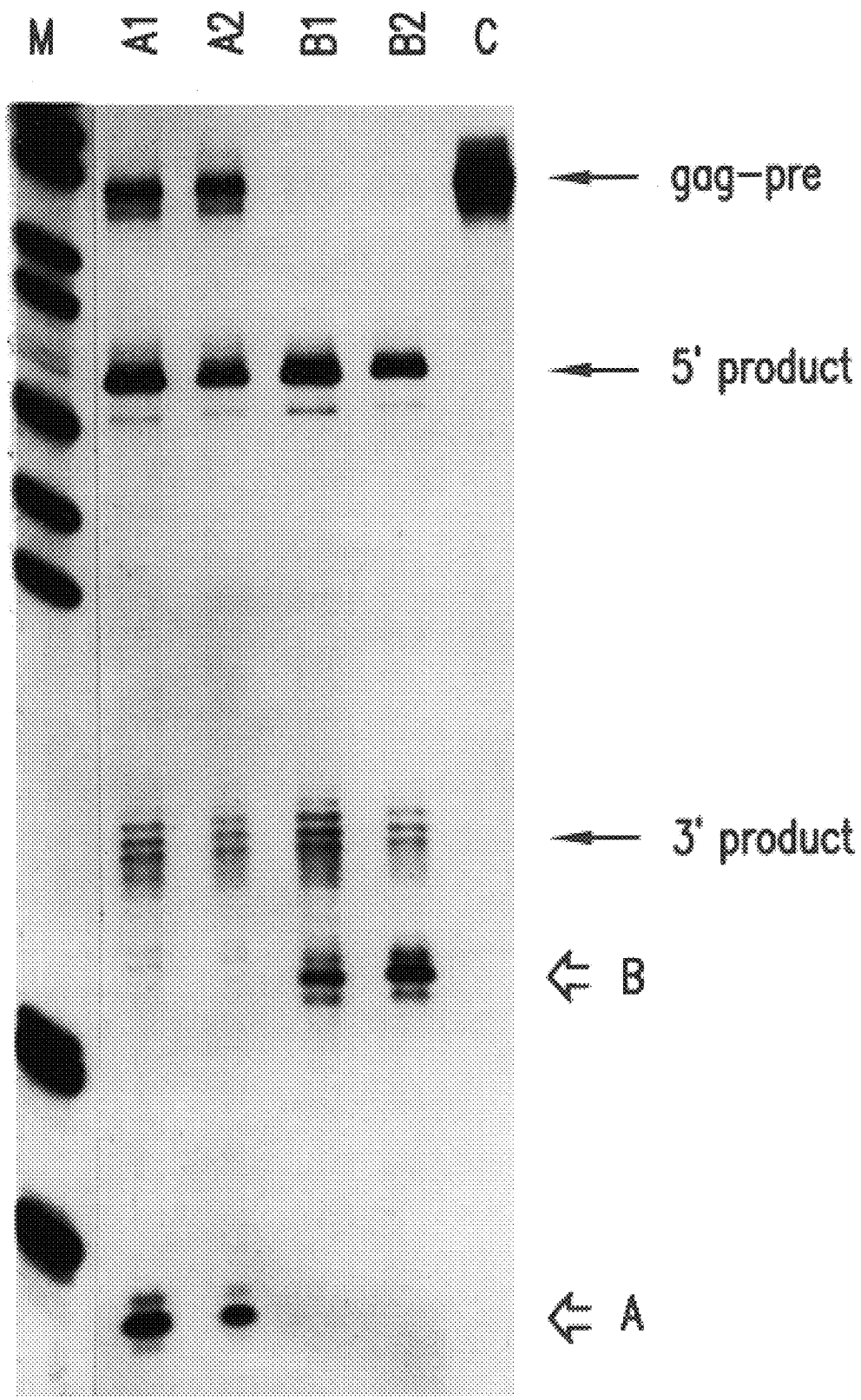
FIG. 8 is a copy of an autoradiograph which shows the HIV-1 RNA in vitro cleavage reaction products formed with the ribozymes of FIGS. 1 and 2.

The reaction mixtures were electrophoresed in a denaturing polyacrylamide gel and the gels were autoradiographed. FIG. 8 is a copy of the autoradiograph which depicts HIV-1 cleavage products formed with the ribozymes of FIGS. 1 and 2. On FIG. 8, lane M includes molecular weight markers derived from Hpa II digested pBR322 DNA; lane A1 depicts the cleavage products of ribozyme A (FIG. 1) not capped during in vitro transcription with GpppG; lane A2 depicts the cleavage products of ribozyme A (FIG. 1) with capped GpppG; lane B1 depicts the cleavage products of ribozyme B (FIG. 2) not capped; lane B2 depicts the cleavage products of ribozyme B capped; lane C depicts the HIV-1 substrate per se incubated under otherwise identical conditions. The positions of the ribozymes (A and B), the substrate (gag-pre) and 5' and 3' products are indicated.

Figure 9:
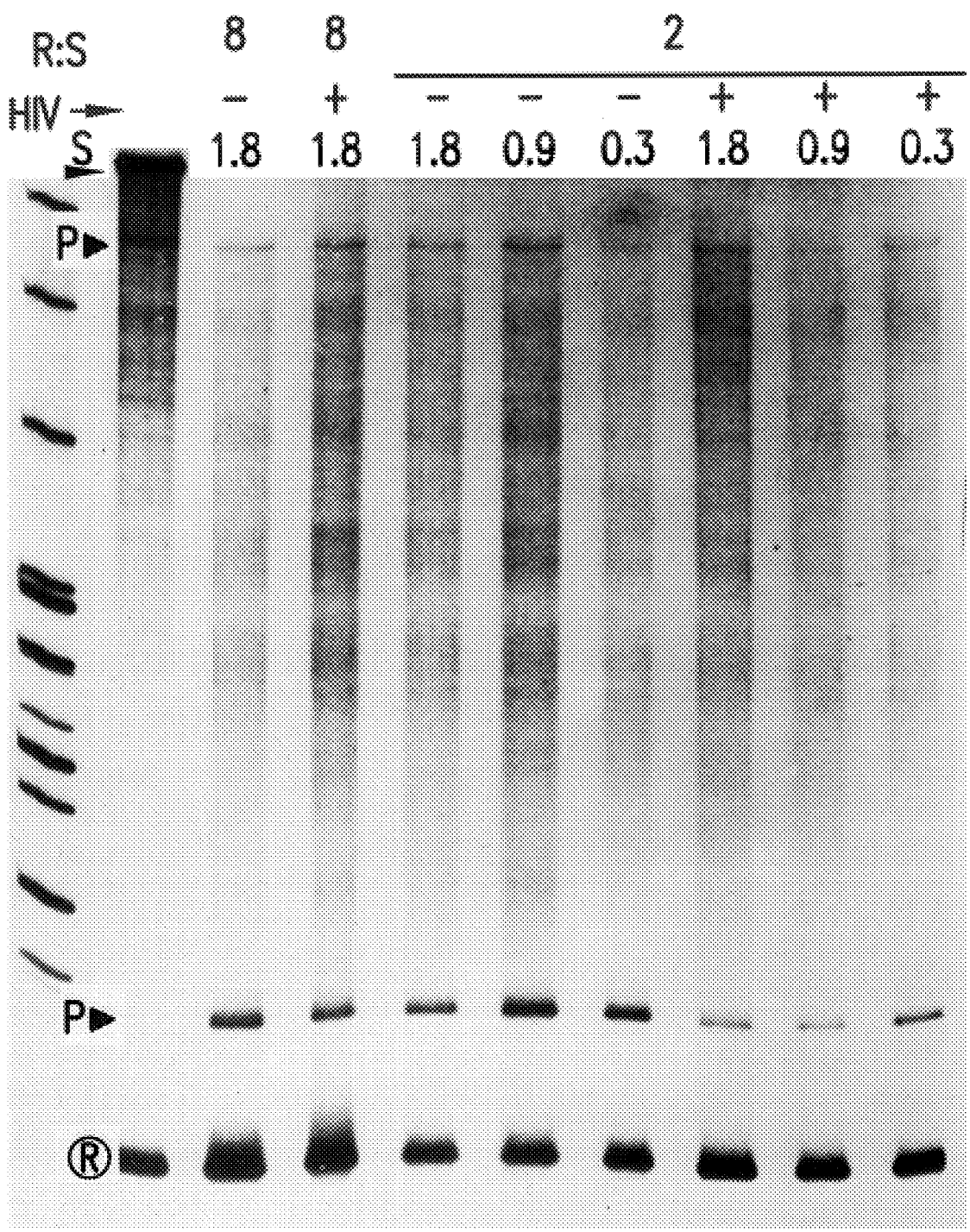
FIG. 9 is a copy of an autoradiograph of the in vitro cleavage reaction products of HIV-1 RNA formed with the ribozyme shown in FIG. 4.

FIG. 9 is a copy of an autoradiograph of the HIV RNA cleavage reaction products formed with the ribozyme shown in FIG. 4. The FIG. 4 ribozyme, in common with ribozymes expressed from a promotor in a living cell, has flanking 5' and 3' sequences. To determine whether or not such flanking sequences interfere with its catalytic activities, the ribozyme of FIG. 4 was tested in vitro against a 620 nucleotide HIV-1 gag region substrate. In addition to the substrate, varying amounts of total RNA prepared from H9 lymphocytes which were either uninfected or infected with HIV-1, were added to the ribozyme reaction to simulate a complex in vivo milieux. Two different ratios of ribozymes to input target RNA (R:S) were utilized as indicated by FIG. 9. More particularly, as the Figure indicates, the amounts of total RNA from either HIV-1 infected or uninfected cells range from 0.3 to 1.8 $\mu$g. In the Figure, the HIV-1 substrate is indicated "S", the cleavage products "P" and the catalytic RNA strand "R".

It appears from the Figure that the extra flanking sequencing did not inhibit cleavage of target sequences and that increasing amounts of RNA from uninfected H9 cells had little or no effect on the cleavage reaction.

A "+" sign above a lane indicates that cellular RNA from HIV-1 infected H-9 cells was added to the reaction. A "−" sign above a lane indicates that uninfected H-9 cellular RNA was added. The numbers above each lane indicate in micrograms the amounts of total cellular RNA added.

EXAMPLE III

Greater Than Stoichiometric Substrate Cleavage

Catalytic RNAs which function as ribozyme components are distinguished from other classes of antisense RNAs by the ability to process excess molar amounts of substrate. This example illustrates the cleavage of greater than stoichiometric amounts of substrate by the catalytic RNA strands of FIGS. 2 and 5.

In these experiments the ratios of substrate to catalytic strand were varied from 1:1 to 50:1. Incubation with large molar excesses of substrate resulted in catalytic cleavage of greater than stoichiometric amounts of substrate over the 14 hour at 37° C. incubation period. Reaction conditions were otherwise the same as described with respect to FIG. 9.

Figure 10:
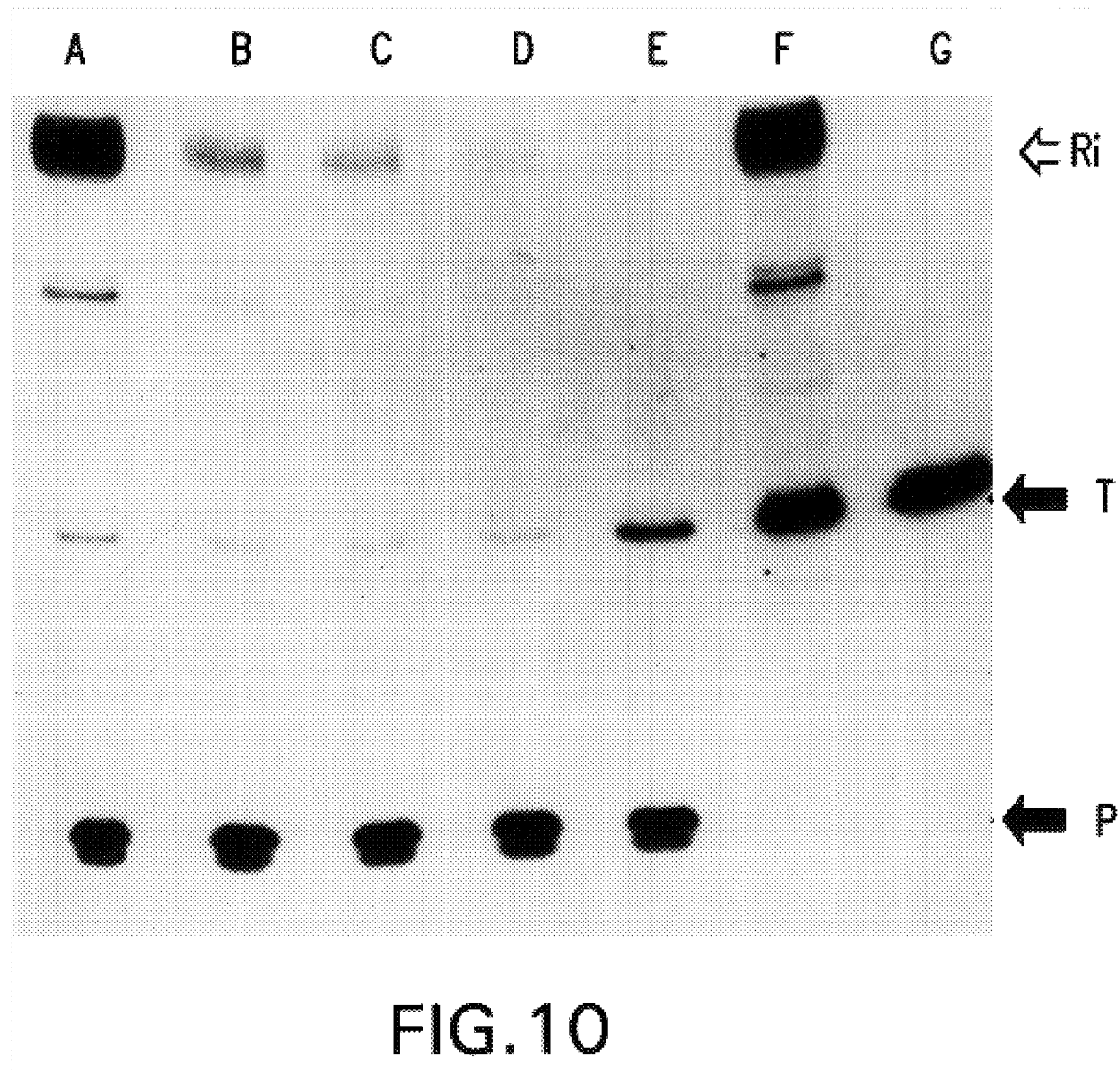
FIG. 10 is a copy of an autoradiograph which indicates substrate turnover of the ribozyme of FIG. 5.

The autoradiograph of FIG. 10 illustrates the results obtained with the catalytic RNA included in the ribozymes of FIG. 5. In each case the catalytic RNA was titrated relative to a fixed amount of template such that the target to catalytic RNA ratios were: lane A 1:1; lane B, 5:1; lane C, 10:1; lane D, 20:1; lane E, 50:1; lane F catalytic RNA plus substrate, no Mg++; lane G, template alone, no catalytic RNA, plus Mg++.

EXAMPLE IV

Transfection of Ribozyme into CD4 Bearing HeLa Cells

Example I describes the cloning of the ribozyme of FIG. 4 into the expression vector of FIG. 7. The cloned ribozyme was transfected into CD4+HeLa cells by lipofection techniques. See, e.g., Felgner, et al., *Proc.Natl.Acad.Sci.U.S.A.* 84:7413–7417 (1987).

The ribozyme gene transfected into CD4+ HeLa cells was assayed for expression into RNA by the polymerase chain reaction (PCR) assay, as described in copending application Serial No. 143,045, using a primer complementary to a sequence in the SV40 portion of the vector in FIG. 7, as well as a primer bearing the same sequence as the 5' end of the catalytic RNA strand itself. The PCR amplified products were detected by a probe complementary to the 3' region of the catalytic RNA strand. The PCR primer sequences were 5'GGATCCGCTTAATACTCGAGTCCTGTAGG 3' (complementary to 5' end of catalytic strand) and 5'CATCAATGTATCTTATC 3' (complementary to SV40).

The sequence of the probe was 5'CCGGATCCGGTGC-GAGAGCGTTTCGTCCTACAGGAC 3' (complementary to 3' end of catalytic strand).

To produce the PCR amplification products, 0.5 $\mu$gms of total cellular RNA in the presence of 50 pmoles of each PCR primer was heated to 94° C. for 5 mins. and cooled slowly to 37° C. Reverse transcription was then conducted at 37° C. for 3 mins. using 2 units of AMV reverse transcriptase. Thereafter, 30 cycles of Taq PCR polymerase mediated amplification were carried out by denaturing at 94° C. for 1 min., annealing at 45° C. for 1 min. and polymerizing at 72° C. for 1 min. 30 sec.

EXAMPLE V

Biological Activity

The transfected CD4+ HeLa cells described in Example IV were assayed to determine the presence or absence of biological activity indicative of the presence of the ribozyme of FIG. 4. CD4+ HeLa cells expressing the ribozyme were infected with HIV-1, and assayed on gag 7 post-infection for HIV-1 p24 gag antigen. These assays involve standard immune precipitation of HIV-1 encoded antigens, utilizing commercially available antibodies supplied by E.I. DuPont de Nemours Corporation. Ribozyme expressing clones which showed reductions in HIV-1 antigens relative to non-ribozyme expressing clones are reported in Table II.

TABLE II

| Cell Line | gag (p24) ng/ml of cell culture media supernatant | (% control) |
| --- | --- | --- |
| HeLa CD4+ (parental cell line) | 1.0 | (100) |
| AI-30 (transfectant) | 0.04 | <4 |
| Pooled clones A + B (transfectant) | 0.23 | <23 |

Therapeutic Procedures

The therapy utilizing the ribozymes of this invention may be directed at HIV-1, HIV-2 or any viral RNA for which nucleotide sequence information is available. Therapeutic use of ribozymes to inactivate endogenous cellular sequences is also covered by this invention. This includes any endogenous gene product which may be deleterious to the host organism. Ribozymes can be delivered to the appropriate cells utilizing targeted liposomes. This can be accomplished with either free ribozyme, or DNA encoding the ribozyme with appropriate transcriptional control signals flanking the ribozyme gene such as depicted in FIG. 4. Alternatively, ribozyme genes can be delivered to pluripotent stem cells via either cellular transfection methods (calcium phosphate, lipofection or electroporation) or via retroviral vectors. The cells are reintroduced into the patient using established methods of autologous bone marrow transplantation. The cells harboring ribozymes active against viral pathogens will have a selective advantage over non-expressing cells since the pathogens will be incapable of propagating in these cells.

More particularly, this invention includes bone marrow stem cells transfected with a ribozyme which cleaves HIV-1 RNA and the use of such transfected stem cells to develop HIV-1 resistant immune systems in AIDS patients.

I claim:

1. A mammalian cell transformed in vitro with a ribozyme as depicted by FIG. 1, FIG. 2, FIG. 3, FIG. 4, or FIG 5.

2. A mammalian cell transformed in vitro with a ribozyme as depicted by FIG. 4.

3. A ribozyme containing expression product of a cell as defined by claim 1.

4. A recombinant expression vector containing a promoter, a gene encoding a ribozyme as depicted by FIGS. 1–5, a transcriptional terminator and a poly A addition site.

5. A mammalian cell transformed in vitro with a vector as defined by claim 4.

6. A HIV-I infected HeLa cell transformed with a ribozyme as depicted by FIG. 4.

Figure 3:
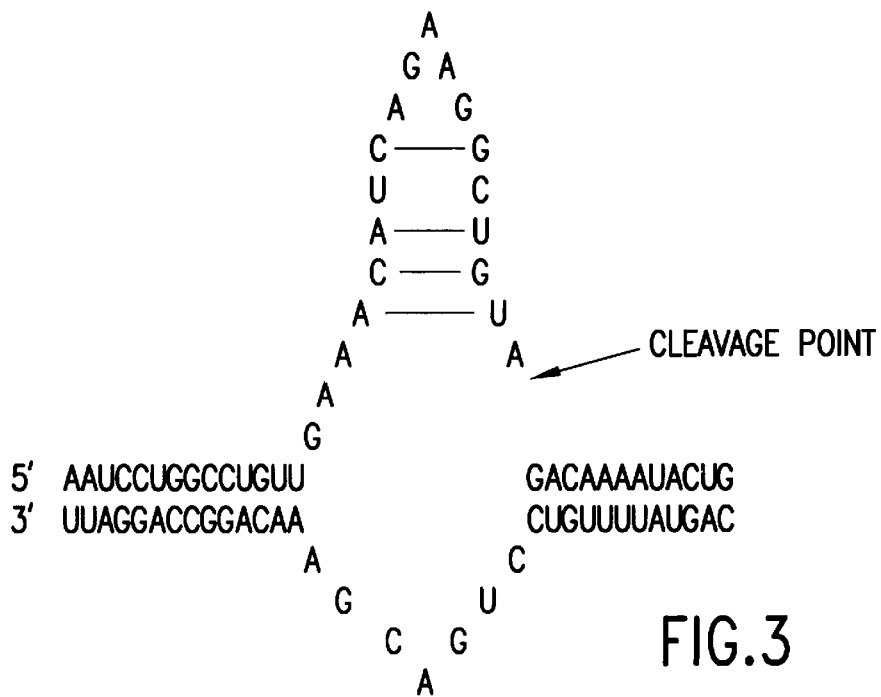
FIG. 3 illustrates the a third ribozyme associated with another cleavage point in the gag region of HIV-1.

7. An HIV-I infected HeLa cell transformed with a ribozyme as depicted by FIG. 1, FIG. 2, or FIG. 3.

8. An expression product of a HeLa cell infected with HIV-I and transformed with a ribozyme as depicted by FIG. 4, said expression product containing said ribozyme.

9. An HIV-I infected HeLa cell transformed with a ribozyme as depicted by FIG. 4, said ribozyme cleaving HIV-I gag transcripts in vitro.

10. A recombinant expression vector as defined by claim 4 containing a gene encoding a ribozyme as depicted by FIG. 4.

* * * * *